United States Patent [19]
Watson

[11] Patent Number: 4,837,355
[45] Date of Patent: Jun. 6, 1989

[54] PROCESS FOR THE SYNTHESIS OF PHENOXYALKANE DERIVATIVES

[75] Inventor: Keith G. Watson, Victoria, Australia

[73] Assignee: ICI Australia Limited, Melbourne, Australia

[21] Appl. No.: 367,229

[22] PCT Filed: Jul. 31, 1981

[86] PCT No.: PCT/AU81/00101
§ 371 Date: Mar. 31, 1982
§ 102(e) Date: Mar. 31, 1982

[87] PCT Pub. No.: WO82/00639
PCT Pub. Date: Mar. 4, 1982

[30] Foreign Application Priority Data
Aug. 21, 1980 [AU] Australia ............... PE5159
Mar. 27, 1981 [AU] Australia ............... PE8174

[51] Int. Cl.[4] .................................. C07C 69/76
[52] U.S. Cl. ........................................ 560/061
[58] Field of Search ............................. 560/61

[56] References Cited
U.S. PATENT DOCUMENTS
3,717,669  2/1973  Grant ................... 560/61

OTHER PUBLICATIONS
E. E. Gilbert, "Sulfonation and Related Reactions", (Interscience, New York, 1965), see pp. 379–381, especially p. 380 lines 19 to 22.
"The Merck Index" 9th ed. (Merck, New Jersey 1976), see page ONR-27, Elbs Persulfate Oxidation.
Tetrahedron, vol. 26 (1970), Pergamon Press, pp. 5945 to 5951, Ogata et al., "Kinetics and Orientation in the Peroxy Disulfate Oxidation of Phenol".

Primary Examiner—Paul J. Killos
Attorney, Agent, or Firm—Cushman, Darby & Cushman

[57] ABSTRACT

The invention concerns a process for the synthesis of a compound of formula I

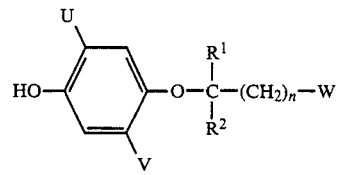

wherein: U and V may be chosen from a range of substituents including hydrogen, halogen, alkyl and alkoxy; $R^1$ and $R^2$ may be chosen from a range of substituents including hydrogen and alkyl; n is 0, 1 or 2; and W may be chosen from a range of substitutents including the group

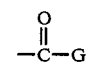

which may be a free carboxylic acid or derivative thereof;
the process comprising reacting a sulfate ester of formula II, wherein Q is a cation, with a compound of formula III, wherein L is a leaving group

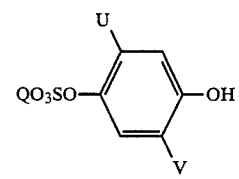

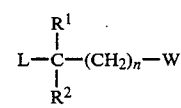

and hydrolyzing the sulfate ester formed. Preferably the sulfate ester of formula II is prepared by the oxidation of a phenol of formula IV with a persulfate.

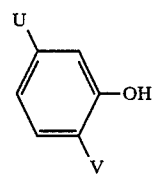

10 Claims, No Drawings

PROCESS FOR THE SYNTHESIS OF PHENOXYALKANE DERIVATIVES

TECHNICAL FIELD

This invention relates to a process for the synthesis of organic compounds and in particular to a process for the synthesis of (4-hydroxyphenoxy)alkane derivatives.

BACKGROUND ART (4-Hydroxyphenoxy)alkane derivatives such as, for example, alkyl 2-(4-hydroxyphenoxy)propionates, are useful intermediates for the synthesis of a wide range of (aryloxyphenoxy)alkane derivatives which have been shown to have herbicidal activity. In the past the required (4-hydroxyphenoxy)alkane derivatives have been prepared either:

(i) by condensing the appropriate 4-alkoxyphenol with the appropriate alkane derivative to give a (4-alkoxyphenoxy)alkane derivative and then cleaving the alkyl residue from the 4-alkoxy group; or (ii) by condensing the appropriate hydroquinone with the appropriate alkane derivative.

However, both of these processes suffer the disadvantage advantage of using relatively expensive hydroquinone (derivatives) and the first process suffers the additional disadvantage of requiring the use of relatively expensive reagents to cleave the alkyl residue from the 4-alkoxy group.

DISCLOSURE OF INVENTION

It has now been found that (4-hydroxyphenoxy)alkane derivatives may be prepared from the appropriate phenol obviating the need to use a hydroquinone or a 4-alkoxyphenol.

Accordingly the invention provides a process for the synthesis of a compound of formula I

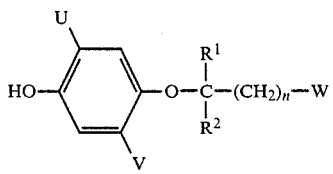

wherein:

U and V are independently chosen from the group consisting of hydrogen, halogen, nitro, cyano, thiocyano, $C_1$ to $C_6$ alkyl, $C_1$ to $C_6$ haloalkyl, $C_2$ to $C_6$ alkenyl, $C_2$ to $C_6$ haloalkenyl, $C_1$ to $C_6$ alkoxy, $C_1$ to $C_6$ haloalkoxy, $C_1$ to $C_6$ alkylthio, carboxy, ($C_1$ to $C_6$ alkoxy)carbonyl, phenyl, phenoxy, phenylthio and the groups substituted phenyl, substituted phenoxy and substituted phenylthio wherein in each group the phenyl ring is substituted with from 1 to 3 substituents chosen from the group consisting of halogen, nitro, cyano, $C_1$ to $C_6$ alkyl, $C_1$ to $C_6$ haloalkyl and $C_1$ to $C_6$ alkoxy;

$R^1$ is chosen from the group consisting of hydrogen, $C_1$ to $C_6$ alkyl, $C_2$ to $C_6$ alkenyl, $C_2$ to $C_6$ alkoxyalkyl, $C_1$ to $C_6$ haloalkyl, acetyl, propionyl and $C_2$ to $C_6$ alkoxycarbonyl, carbonyl, $R^2$ is chosen from the group consisting of hydrogen, $C_1$ to $C_6$ alkyl, $C_2$ to $C_6$ alkenyl, $C_2$ to $C_6$ alkoxyalkyl and $C_1$ to $C_6$ haloalkyl, or $R^1$ and $R^2$ together may form a methylene, ethylidene, propylidene or isopropylidene group;

W is chosen from the group consisting of cyano, thiocarbamoyl,

and $CH_2Z$ wherein: G is chosen from the group consisting of hydroxy, mercapto, $C_1$ to $C_{10}$ alkoxy, $C_1$ to $C_{10}$ haloalkoxy, $C_2$ to $C_{10}$ alkenyloxy, $C_2$ to $C_{10}$ alkynyloxy, $C_1$ to $C_{10}$ alkylthio, $C_2$ to $C_{10}$ alkenylthio, $C_2$ to $C_{10}$ alkynylthio, $C_3$ to $C_7$ cycloalkoxy, $C_3$ to $C_7$ cycloalkoxy substituted with 1 or 2 $C_1$ to $C_4$ alkyl groups, phenoxy, phenylthio, benzyloxy, benzylthio, the group $C_1$ to $C_{10}$ alkoxy substituted with a substituent chosen from the group consisting of $C_1$ to $C_6$ alkoxy, amino, ammonio, cyano, N-($C_1$ to $C_6$ alkyl)amino, N,N-di($C_1$ to $C_6$ alkyl)amino and N,N,N-tri($C_1$ to $C_6$ alkyl)ammonio, the groups phenoxy, phenylthio, benzyloxy and benzylthio wherein in each group the phenyl ring is substituted with from 1 to 3 substituents chosen from the group consisting of halogen, nitro, cyano, $C_1$ to $C_6$ alkyl, $C_1$ to $C_6$ haloalkyl and $C_1$ to $C_6$ alkoxy, the group OM wherein M is the cation of an inorganic or organic base, the group $-NHSO_2R^3$ wherein $R^3$ is chosen from $C_1$ to $C_{10}$ alkyl and $C_1$ to $C_6$ haloalkyl, the group $-NR^4R^5$ wherein $R^4$ and $R^5$ are independently chosen from the group consisting of hydrogen, $C_1$ to $C_6$ alkyl, phenyl and benzyl or $R^4$ and $R^5$ together form a heterocyclic ring, and the group $-O-N=R^6$ wherein $R^6$ is a $C_1$ to $C_{10}$ alkylidene group;

Z is chosen from the group consisting of halogen, hydroxy, mercapto, $C_1$ to $C_{10}$ alkoxy, $C_1$ to $C_{10}$ haloalkoxy, $C_1$ to $C_{10}$ alkylthio and the group $-NR^4R^5$ wherein $R^4$ and $R^5$ are as heretofore defined; and n is 0, 1 or 2;

which process is characterised in that is comprises comprises the following steps in sequence:

(a) reacting a sulfate ester of formula II,

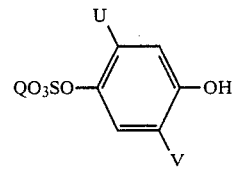

wherein Q is a cation, with a compound of formula III,

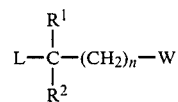

wherein L is a leaving group; and (b) hydrolysing the sulfate ester formed in step (a) to give a compound of formula I.

The sulfate ester of formula II may be readily formed by the oxidation of a phenol with persulfuric acid or a salt thereof. Accordingly, in a preferred embodiment the invention provides a process for the synthesis of a compound of formula I as hereinbefore defined which process comprises:

(i) oxidizing a compound of formula IV

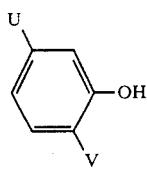

with persulfuric acid or a salt thereof to form a sulfate ester of formula II,

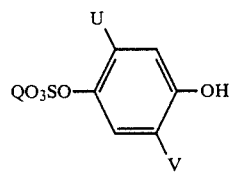

wherein Q is a cation; and
(ii) which process is characterized by the following steps in sequence:
(a) reacting the sulfate ester of formula II with a compound of formula III,

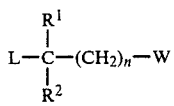

wherein L is a leaving group; and
(b) hydrolysing the sulfate ester formed in step a) to give a compound of formula I.

The compounds of formula I wherein $R^1$ and $R^2$ are not the same, are optically active and the present invention also includes a process for the preparation of the individual stereo isomers of such compounds, and mixtures of those stereo isomers in addition to the racemic mixture of stereo isomers.

When W is the group

wherein G is the group OM and M is the cation of an inorganic or organic base, suitable inorganic bases include the alkali and alkaline earth metal hydroxides and carbonates, and ammonia and suitable organic bases include amines of the formula $NR^7R^8R^9$ wherein $R^7$, $R^8$ and $R^9$ are independently chosen from the group consisting of hydrogen, $C_1$ to $C_6$ alkyl, $C_1$ to $C_6$ hydroxyalkyl, phenyl and benzyl.

When W is chosen from the group

and $-CH_2Z$ wherein G or Z is the group $NR^4R^5$ and $R^4$ and $R^5$ together form a heterocyclic ring, suitable heterocyclic groups include 1-pyrrolyl, 1-imidazolyl, 1-pyrazolyl, 1-pyrrolidinyl, 1-imidazolidinyl, 1-pyrazolidinyl, 1-piperidyl, 1-piperazinyl and 4-morpholinyl.

The nature of the cation Q in the compound of formula II is not critical. Suitable Q include the hydrogen ion, the alkali and alkaline earth metal ions and the ammonium ion.

The nature of the leaving group L in the compound of formula III is not critical. For example, suitable leaving groups may be chosen from halogen, $C_1$ to $C_6$ alkylsulfonyl, $C_1$ to $C_6$ haloalkylsulfonyl, arylsulfonyl such as benzenesulfonyl, aralkylsulfonyl such as benzylsulfonyl, alkarylsulfonyl such as p-toluenesulfonyl, $C_1$ to $C_6$ alkylsulfonyloxy, $C_1$ to $C_6$ haloalkylsulfonyloxy, arylsulfonyloxy such as benzenesulfonyloxy, aralkysulfonyloxy such as benzylsulfonyloxy, alkarylsulfonyloxy such as p-toluenesulfonyloxy, $C_1$ to $C_6$ alkylsulfonamido, $C_1$ to $C_6$ haloalkylsulfonamido and the group $-N\oplus R^{10}R^{11}R^{12}X\ominus$ wherein $R^{10}$, $R^{11}$ and $R^{12}$ are chosen from $C_1$ to $C_6$ alkyl, phenyl and benzyl or $-NR^{10}R^{11}R^{12}$ is a heterocyclic group such as, for example, 1-methyl-1-pyrrolio, 1-methyl-1-imidazolio, 1-methyl-1-pyrrolidinio, 1-methyl-1-pyrrolinio, 1-methyl-1-imidazolinio, 1-methyl-1-piperidinio, 4-methyl-4-morpholinio, 1-pyridinio, 1-pyrazinio, 1-pyrimidino and 1-pyridazinio, and $X\ominus$ is a suitable anion including the anions of strong acids such as, for example, hydrochloric acid, hydrobromic acid, hydriodic acid, tetrafluoroboric acid, hexafluorophosphoric acid, hexafluoroantimonoic acid, methansulfonic acid, fluorosulfonic acid, fluoromethanesulfonic acid and trifluoromethanesulfonic acid.

In the compound of formula I: Preferred U and V include hydrogen, halogen, nitro, cyano, $C_1$ to $C_6$ alkyl, $C_1$ to $C_6$ haloalkyl and $C_1$ to $C_6$ alkoxy. More preferred U and V include hydrogen and halogen.

Preferred $R^1$ and $R^2$ include hydrogen and $C_1$ to $C_6$ alkyl. More preferred $R^1$ is methyl and more preferred $R^2$ is hydrogen.

Preferred W is the group

wherein G is chosen from the group consisting of hydroxy, $C_1$ to $C_{10}$ alkoxy, $C_1$ to $C_{10}$ haloalkyoxy, $C_2$ to $C_{10}$ alkenyloxy, $C_2$ to $C_{10}$ alkynyloxy, $C_1$ to $C_{10}$ alkylthio, $C_2$ to $C_{10}$ alkenylthio, $C_2$ to $C_{10}$ alkynylthio, phenoxy, benzyloxy, cyclohexyloxy, the group $C_1$ to $C_{10}$ alkoxy substituted with a substituent chosen from the group consisting of $C_1$ to $C_6$ alkoxy, amino, N-($C_1$ to $C_6$ alkyl)amino, N,N-di($C_1$ to $C_6$ alkyl)amino and N,N,N-tri($C_1$ to $C_6$ alkyl)ammonio, the group $NR^4R^5$ wherein $R^4$ and $R^5$ are independently chosen from hydrogen, $C_1$ to $C_6$ alkyl, $C_1$ to $C_6$ hydroxyalkyl, $C_1$ to $C_6$ haloalkyl, and phenyl, the group OM wherein M is an alkali metal ion, alkaline earth metal ion or an ammonium ion $HNR^7R^8R^9$ wherein $R^7$, $R^8$ and $R^9$ are independently chosen from the group consisting of hydrogen, $C_1$ to $C_6$ alkyl, $C_1$ to $C_6$ hydroxyalkyl, phenyl and benzyl, the group $-NHSO_2R^3$ wherein $R^3$ is a $C_1$ to $C_6$ alkyl, and the group $-O-N=R^6$ wherein $R^6$ is a $C_1$ to $C_{10}$ alkylidene group.

More preferred W is the group

wherein G is chosen from the group consisting of hydroxy, $C_1$ to $C_{10}$ alkoxy, $C_2$ to $C_{10}$ alkenyloxy, $C_2$ to $C_{10}$ alkynyloxy and the group OM wherein M is an alkali metal or alkaline earth metal ion. Preferred n is O.

In the compound of formula II preferred Q include the alkali metals such as, for example, sodium and potassium, and ammonium.

In the compound of formula III preferred L include the halogen atoms chlorine, bromine and iodine, methanesulfonyl, trifluoromethanesulfonyl, p-toluenesulfonyl, methanesulfonyloxy, trifluoromethanesulfonyloxy, p-toluenesulfonyloxy, trifluoromethanesulfoamido and 1-pyrimidino p-toluenesulfonate.

Step a) of the process of the invention may be carried out under a wide range of operating conditions. Preferably the reaction is carried out in the presence of an alkaline material.

Suitable alkaline materials include the alkali metal and alkaline earth metal hydroxides and carbonates such as, for example, sodium hydroxide, potassium hydroxide, sodium carbonate and potassium carbonate.

Step a) of the process of the invention is also preferably carried out in the presence of an organic solvent. Suitable solvents include: alcohols such as, for example, methanol, ethanol, n-propanol and isopropanol; ketones such as, for example, acetone, methyl ethyl ketone and methyl isobutyl ketone; and dipolar aproptic solvents such as, for example, dimethylformamide, dimethylacetamide, dimethylsulfoxide, N-methylpyrrolidone, hexamethylphosphoramide and sulfolan.

The specific reaction conditions required to effect the reaction in step a) of the process of the invention will vary with the specific reactants and solvent used. In general the reaction is facilitated by the application of heat and usually a reaction temperature in the range of form 40° to 150° C. and a reaction time of between 0.5 and 20 hours is satisfactory. However, higher or lower reaction temperatures and/or shorter or longer reaction times may be employed if desired.

On completion of the reaction in step (a) of the process of the invention the compound of formula I may be formed by hydrolysis of the sulfate ester according to step b) of the process of the invention. The sulfate ester formed in step (a) of the process of the invention may be hydrolysed without isolation from the reaction mixture, or alternatively the sulfate ester may be isolated from the reaction mixture and then hydrolysed.

If step (b) of the process of the invention is carried out without the isolation of the sulfate ester, conveniently, the compound of formula I may be formed in situ by acid hydrolysis. For example, the reaction mixture formed in step (a) of the process of the invention may be acidified, for example with a mineral acid, for example, hydrochloric acid or an organic acid, for example, acetic acid, to hydrolyse the sulfate ester. In general the hydrolysis reaction is facilitated by the application of heat.

Alternatively, the sulfate ester formed in step (a) of the process of the invention may be isolated from the reaction mixture before hydrolysis. Conveniently, the sulfate ester may be isolated by removing the solvent from the reaction mixture formed in step (a) of the process of the invention. For example, if step (a) of the process of the invention was carried out in aqueous solution the reaction mixture may be extracted with a water-immiscible organic solvent, optionally after acidification of the reaction mixture, to remove any unreacted compound of formula III from the reaction mixture. The solvent may then be removed from the aqueous solution, for example by distillation, distillation under reduced pressure, evaporation or freeze-drying, and the sulfate ester may be purified as required. The sulfate ester may then be hydrolysed to form a compound of formula I, for example, by hydrolysis with an aqueous mineral acid such as hydrochloric acid or an organic acid such as acetic acid.

Preferably, the sulfate ester of formula II which is used in step (a) of the process of the present invention is formed by the oxidation of a phenol of formula IV with persulfuric acid or a salt thereof. The oxidation may be carried out under a wide range of operating conditions. However, preferably the oxidation is carried out in aqueous alkaline solution using a salt of persulfuric acid. Suitable bases include the alkali metal and alkaline earth metal oxides, hydroxides and and carbonates. Suitable salts of persulfuric acid include the ammonium salt and the alkali metal salts such as sodium persulfate and potassium persulfate. Conveniently, the compound of formula IV is dissolved in an aqueous alkaline solution and the oxidizing agent is added slowly to the solution which is maintained at or below ambient temperature during the addition.

On completion of the oxidation process the sulfate ester of formula II may be reacted directly, without isolation, with the compound of formula III or alternatively the sulfate ester may be isolated from the reaction mixture and then reacted with the compound of formula III.

If the step (a) of the process of the invention is carried out without isolation of the sulfate ester, conveniently, the compound of formula III may be simply added to the oxidation reaction mixture and step a) of the process may be carried out in the reaction mixture formed in the oxidation process. If desired, any unreacted compound of formula IV may be removed from the oxidation reaction mixture before carrying out step a) of the process of the invention by, for example, acidifying the aqueous reaction mixture formed (eg by the addition of an acid or carbon dioxide) and extracting the aqueous acid solution with a relatively polar, waterimmiscible organic solvent. Any unreacted compound of formula IV extracted into the organic solvent may be recovered and recycled.

Alternatively, the sulfate ester of formula II formed in the oxidation process may be isolated before reaction with the compound of formula III. Conveniently, the sulfate ester may be isolated by removing the solvent from the reaction mixture formed in the oxidation process and extracting the sulfate ester from the residue. For example, the aqueous reaction mixture formed may be acidified (eg by the addition of an acid or carbon dioxide) and extracted with a relatively polar, waterimmiscible organic solvent to remove any unreacted compound of formula IV from the reaction mixture. The aqueous phase may then be made basic, for example made alkaline to litmus with sodium hydrogen carbonate. The solvent may then be removed from the alkaline solution, for example by distillation, distillation under reduced pressure, evaporation or freeze-drying, and the sulfate ester may then be extracted from the residue. The solvent used to extract the sulfate ester from the residue will depend to a large extent on the solubility properties of the sulfate ester. However, in general the solvent used will be a polar organic solvent, such as, for example, ethanol or acetone, in order to effect maximum recovery of the sulfate ester combined with as small an amount of inorganic salts as possible. After extraction of the sulfate ester, the sulfate ester containing solution may be used directly in step (a) of the process of the invention or the sulfate ester may be separated for example by removal of the solvent, and further purified as required.

The process of the invention is particularly suitable for the preparation of compounds of formula I wherein n is 0 and W is the group

that is compounds of formula V.

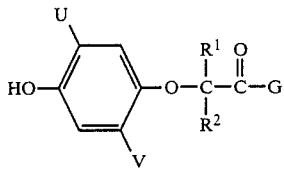

For example, 2-(4-hydroxyphenoxy)propionate may be prepared by:
(a) reacting a 4-hydroxyphenylsulfate salt with a 2-halopropionic acid or a derivative thereof; and
(b) hydrolysing the sulfate ester formed in step a) to give the 2-(4-hydroxyphenoxy)propionate.

Preferably the 2-(4-hydroxyphenoxy)propionate is prepared by oxidizing phenol with a persulfate salt in aqueous alkaline solution to give a 4-hydroxyphenylsulfate salt and
(a) reacting the 4-hydroxyphenylsulfate salt with a 2-halopropionic acid or a derivative thereof; and
(b) hydrolysing the sulfate ester formed in step (a) to give the 2-(4-hydroxyphenoxy)propionate.

If desired the 2-(4-hydroxyphenoxy)propionate may be converted to another propionic acid derivative such as an acid salt, acid ester, acid amide, acid halide, nitrile, alcohol or alkyl halide utilizing methods known in the art for the preparation of carboxylic acid derivatives.

MODES OF CARRYING OUT THE INVENTION

The invention is now illustrated by, but in no way limited to, the following Examples.

EXAMPLE 1

Preparation of Ethyl 2-(4-hydroxyphenoxy)propionate

A solution of potassium persulfate (27 g, 0.1 mole) in water (500 ml) was added slowly to a stirred solution of phenol (9.4 g, 0.1 mole) in aqueous 10% sodium hydroxide (200 ml) which was maintained at or below a temperature of 20° C. throughout the addition. After stirring for a period of 36 hours at room temperature the solution was acidified to pH 4.0 (Congo red) using concentrated hydrochloric acid and the acidic solution was extracted with diethyl ether (2 x 500 ml). The aqueous phase was made alkaline with sodium hydroxide and the water was removed by distillation under reduced pressure to give a solid residue. The residue was acidified and extracted with aqueous 90% ethanol (500 ml). The aqueous ethanolic solution was made strongly basic and then heated under reflux while ethyl 2bromopropionate (18 g, 0.1 mole) was added dropwise. After heating under reflux for a period of 2 hours the hot solution was acidified with concentrated hydrochloric acid and then stirred overnight at room temperature. The solvent was removed by distillation under reduced pressure and the residue was dissolved in ethanol (500 ml). Concentrated sulfuric acid (1 ml) was added to the ethanolic solution and the mixture was heated under reflux for a period of 48 hours. The solvent was removed by distillation under reduced pressure and the residue was partitioned between water and dichloromethane. The organic phase was dried (over anhydrous magnesium sulfate) and the solvent was removed by distillation under reduced pressure to give a dark-coloured oil. The crude product was chromatographed over silica gel (eluent dichloromethane) to give ethyl 2-(4-hydroxyphenoxy)propionate as a colour less oil.

the product was characterised by comparison with an authentic sample of ethyl 2-(4-hydroxyphenoxy)propionate. The pmr spectrum of the product was identical with the pmr spectrum of the authentic sample and chromatographic behaviour of the product on thinlayer chromatography was identical with the authentic sample.

EXAMPLE 2

Preparation of Ethyl 2-(4-hydroxyphenoxy)propionate (a) Potassium 4-hydroxyphenylsulfate A solution of potassium persulfate (27.0 g) in water (500 ml) was added dropwise over a period of 2 hours to a stirred solution of phenol (9.4 g) and sodium hydroxide (20.0 g) in water (200 ml) the reaction mixture being maintained at a temperature of 200±2° C. through the addition. On completion of the addition the reaction mixture was stirred for a further period of 24 hours at a temperature of 20° C.

An excess of carbon dioxide was passed through the reaction mixture to neutralize the base. The mixture was then extracted with diethyl ether (2×200 ml) and the unreacted phenol (2.7 g) was recovered from the ethereal extracts. The aqueous solution was evaporated to dryness under reduced pressure and the solid residue was extracted with an ethanol (20 parts)/water (1 part) mixture (3×500 ml). The combined aqueous ethanolic extracts were evaporated to dryness to give potassium 4-hydroxyphenylsulfate as a pale brown powder (10.5 g), mp 210°–220° C. (Found: C, 31.7; H, 2,65; S, 13.9. $C_6H_5O_5SK$ requires: C, 31.6, H, 2.2; S, 14.0%).

(b) Ethyl 2-(4-hydroxyphenoxy) propionate

A mixture of potassium 4-hydroxyphenylsulfate (20.5 g; prepared as described in part a) above), ethyl 2-bromopropionate (21.0 g), anhydrous potassium carbonate (15.0 g) and ethanol (200 ml) was heated under reflux, with stirring, for a period of 6 hours. The ethanol was removed from the reaction mixture by distillation under reduced pressure, acetic acid (150 ml) was added to the solid residue and the mixture was heated under reflux for a period of 2 hours. The acetic acid was removed from the reaction mixture by distillation under reduced pressure and the residue was partitioned between water (200 ml) and chloroform (2 x 500 ml). The combined organic extracts were dried over anhydrous magnesium sulfate and the solvent was removed by distillation under reduced pressure to give ethyl 2-(4-hydroxyphenoxy)propionate (13.1 g; 69%) as a brown oil.

The compound was characterized by comparison with an authentic sample of ethyl 2-(4-hydroxyphenoxy)propionate prepared by a different route. The pmr spectrum of the product was identical with the pmr spectrum of the authentic sample. The infra-red spectrum of the product film; $\nu$ in cm$^{-1}$); 3420, 2980, 1725, 1500, 1442, 1370, 1208, 1130, 1095, 1048, 1012, 943, 825, 755) was identical with the infra-red spectrum of the authentic sample. The chromatographic behaviour of the product on thin-layer chromatography was identical with the authentic sample.

EXAMPLE 3

Preparation of n-Butyl 2-(4-hydroxyphenoxy)propionate

A mixture of potassium 4-hydroxyphenylsulfate (1.14 g; prepared as described in Example 2 part (a)), n-butyl 2-chloropropionate (0.9 g), anhydrous potassium carbonate (0.75 g), dimethylformamide (5 ml) and xylene (5 ml) was heated at a temperature of 100°–110° C., with stirring, for a period of 4 hours. The solvents were removed by distillation under reduced pressure, acetic acid 915 ml) was added to the solid residue and the mixture was heated under reflux for a period of 2 hours. The acetic acid was removed by distillation under reduced pressure and the solid residue was partitioned between water (20 ml) and chloroform (2×50 ml). The combined chloroform extracts were dried over anhydrous magnesium sulfate and the solvent was removed by distillation under reduced pressure to give a brown oil (1.4 g). The product was purified by chromatography over silica gel with chloroform elution to give pure n-butyl 2-(4-hydroxyphenoxy)propionate (0.65 g; 55%) as a colourless oil. Proton magnetic resonance spectrum (CDCl$_3$; $\delta$ in ppm): 0.7–1.7, m, 7H; 1.55, d, 3H; 4.1, t, 2H; 4.65, q, 1H; 6.75, s, 4H.

EXAMPLE 4

Preparation of 2-(4-Hydroxyphenoxy)propionate Acid

A mixture of potassium 4-hydroxyphenylsulfate (1.14 g; prepared as described in Example 2 part (a)), ethyl 2-bromopropionate (0.95 g), anhydrous potassium carbonate (0.7 g) and ethanol (50 ml) was heated under reflux for a period of 3.5 hours. The ethanol was removed by distillation under reduced pressure, acetic acid (50 ml) was added to the solid residue and the mixture was heated under reflux for a period of 2 hours. The acetic acid was removed by distillation under reduced pressure, aqueous 1M sodium hydroxide (100 ml) was added to the solid residue and the mixture was stirred at a temperature of 20° C. for a period of 0.5 hours. The aqueous solution was neutralized by the addition of dilute 2M hydrochloric acid (50 ml) and extracted with ethyl acetate (4×100 ml). The combined ethyl acetate extracts were dried over anhydrous magnesium sulfate and the solvent was removed by distillation under reduced pressure to give 2-(4-hydroxyphenoxy)propionate acid (0.75 g; 82%) as a brown solid, mp 140° C. The product was characterized by esterification in ethanol (sulfuric acid catalysis) to give ethyl 2-(4-hydroxyphenoxy)propionate as a brown oil (0.72 g; 68% overall yield).

EXAMPLE 5

Preparation of Ethyl 2-(2-fluoro-4-hydroxyphenoxy)propionate

Potassium persulphate (27 g, 0.1 mole) was added in portions, as a finely ground powder, over a period of 8 hours, to a stirred solution of 2-fluorophenol (11.2 g, 0.1 mole) and sodium hydroxide (12 g, 0.3 mole) in water (400 ml) at 20° C. The mixture was stirred at 20° F. for 16 hours and then treated with carbon dioxide to bring the pH to 10. Unreacted 2-fluorophenol (3.9 g) was removed by extraction with diethyl ether (3×50 ml). The aqueous layer was concentrated under vacuum to a pale brown powder (45 g) which was placed in a soxhlet and extracted with absolute ethanol (250 ml) for 6 hours. Evaporation of the ethanol gave crude potassium 3-fluoro4-hydroxyphenylsulphate (9.5 g) as a pale brown powder.

A mixture of the crude potassium 3-fluoro-4-hydroxyphenylsulphate (9.5, 0.04 mole), ethyl 2-bromopropionate (8.0 g, 0.044 mole), anhydrous potassium carbonate (5.5 g, 0.04 mole) and ethanol (200 ml) was stirred and refluxed for 5 hours. The ethanol was removed under reduced pressure and the residue was refluxed in acetic acid 9150 ml) for 1.5 hours. The solution was poured into water (400 ml) and extracted with methylene chloride (3×100 ml). The methylene chloride layers were washed with water (300 ml) then dried (MgSO$_4$) and evaporated to give the crude product as a brown oil (7.8 g). Chromatography on silica gel (80 g) with elution by chloroform gave the pure ethyl 2-(2-fluoro-4-hydroxyphenoxy)propionate (5.5 g; 38% overall, taking into account recovered 2-fluorophenol) as a nearly colourless oil. Proton magnetic resonance spectrum (CDCl$_3$; $\delta$ in ppm): 1.3, t, 3H; 1.6, d, 3H; 4.3, q, 2H; 4.7, q, 1H; 6.4–7.1, m, 4H..

INDUSTRIAL APPLICABILITY

The (4-hydroxyphenoxy)alkanes which may be prepared according to the process of the invention are useful intermediates for the synthesis of a wide range of herbicidal (aryloxyphenoxy)alkane derivatives. In particular, the 2-(4-hydroxyphenoxy)propionic acid derivatives which may be prepared according to the process of the invention are useful intermediates in the preparation of a number of herbicidal 2-(4-aryloxyphenoxy)-propionate acid derivatives.

The process of the present invention offers a number of advantages over the prior art processes which have been used for the synthesis of such (4-hydroxyphenoxy)alkane derivatives. In the past the required (4-hydroxyphenoxy)alkane derivatives have been prepared either:

(i) by condensing the appropriate 4-alkoxyphenol with the appropriate alkane derivative to give a (4-alkoxyphenoxy)alkane derivative and then cleaving the alkyl residue from the 4-alkoxy group; or (ii) by condensing the appropriate hydroquinone with the appropriate alkane derivative.

However, both of these processes suffer the disadvantage of using relatively expensive hydroquinone (derivatives). Moreover, the first process suffers the additional disadvantage of requiring the use of relatively expensive reagents to cleave the alkyl residue from the 4-alkoxy group while the second process suffers the additional disadvantage of possible reaction at both hydroxyl groups to give bis(alkane) derivatives of hydroquinones.

It will be evident to those skilled in the art that the process of the present invention offers the advantages of the utilization of relatively inexpensive phenol (derivatives) and does not suffer the disadvantages of either the use of relatively expensive reagents or the possible formation of bis(alkane) derivatives of hydroquinones.

I claim:
1. A process for the synthesis of a compound of formula I

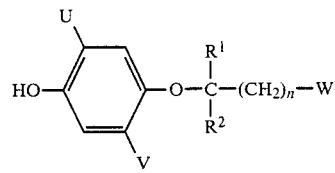

wherein:
U and V are independently chosen from the group consisting of hydrogen, halogen, nitro, cyano, thiocyano, $C_1$ to $C_6$ alkyl, $C_1$ to $C_6$ haloalkyl, $C_2$ to $C_6$ alkenyl, $C_2$ to $C_6$ haloalkenyl, $C_1$ to $C_6$ alkoxy, $C_1$ to $C_6$ haloalkoxy, $C_1$ to $C_6$ alkylthio, carboxy, ($C_1$ to $C_6$ alkoxy)carbonyl, phenyl, phenoxy, phenylthio and the groups substituted phenyl, substituted phenoxy and substituted phenylthio wherein in each group the phenyl ring is substituted with from 1 to 3 substituents chosen from the group consisting of halogen, nitro, cyano, $C_1$ to $C_6$ alkyl, $C_1$ to $C_6$ haloalkyl and $C_1$ to $C_6$ alkoxy;

$R^1$ is chosen from the group consisting of hydrogen, $C_1$ to $C_6$ alkyl, $C_2$ to $C_6$ alkenyl, $C_2$ to $C_6$ alkoxyalkyl, $C_1$ to $C_6$ haloalkyl, acetyl, propionyl and $C_2$ to $C_6$ alkoxycarbonyl, $R^2$ is chosen from the group consisting of hydrogen, $C_1$ to $C_6$ alkyl, $C_2$ to $C_6$ alkenyl, $C_2$ to $C_6$, alkoxyalkyl and $C_1$ to $C_6$ haloalkyl, or $R^1$ and $R^2$ together may form a methylene, ethylidene, propylidene or isopropylidene group;

W is chosen from the group consisting of cyano, thiocarbamoyl,

and $CH_2Z$ wherein: G is chosen from the group consisting of hydroxy, mercapto, $C_1$ to $C_{10}$ alkoxy, $C_1$ to $C_{10}$ haloalkoxy, $C_2$ to $C_{10}$ alkenyloxy, $C_2$ to $C_{10}$ alkynyloxy, $C_1$ to $C_{10}$ alkylthio, $C_2$ to $C_{10}$ alkynylthio, $C_2$ to $C_{10}$ alkynylthio, $C_3$ to $C_7$ cycloalkoxy, $C_3$ to $C_7$ cycloalkoxy substituted with 1 or 2 $C_1$ to $C_4$ alkyl groups, phenoxy, phenylthio, benzyloxy, benzylthio, the group $C_1$ to $C_{10}$ alkoxy substituted with a substituent chosen from the group consisting of $C_1$ to $C_6$ alkoxy, amino, ammonio, cyano, N-($C_1$ to $C_6$ alkyl)amino, N,N-di($C_1$ to $C_6$ alkyl)amino and N,N,N-tri($C_1$ to $C_6$ alkyl)ammonio, the groups phenoxy, phenylthio, benzyloxy and benzylthio wherein in each group the phenyl ring is substituted with from 1 to 3 substituents chosen from the group consisting of halogen, nitro, cyano, $C_1$ to $C_6$ alkyl, $C_1$ to $C_6$ haloalkyl and $C_1$ to $C_6$ alkoxy, the group OM wherein M is the cation of an inorganic or organic base, the group $-NHSO_2R^3$ wherein $R^3$ is chosen from $C_1$ to $C_{10}$ alkyl and $C_1$ to $C_6$ haloalkyl, the group $-NR^4R^5$ wherein $R^4$ and $R^5$ are independently chosen from the group consisting of hydrogen, $C_1$ to $C_6$ alkyl, phenyl and benzyl or $R^4$ and $R^5$ together form a heterocyclic ring, and the group $-O-N=R^6$ wherein $R^6$ is a $C_1$ to $C_{10}$ alkylidene group;

Z is chosen from the group consisting of halogen, hydroxy, mercapto, $C_1$ to $C_{10}$ alkoxy, $C_1$ to $C_{10}$ haloalkoxy, $C_1$ to $C_{10}$ alkylthio and the group $-NR^4R^5$ wherein $R^4$ and $R^5$ are as hereinbefore defined; and n is 0, 1 or 2;

which process is characterized in that it comprises the following steps in sequence;
(a) reacting a sulfate ester of formula II,

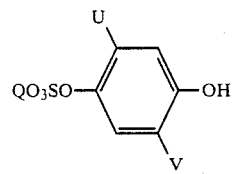

wherein Q is a cation, with a compound of formula III,

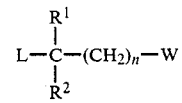

wherein L is a leaving group; and
(b) hydrolysing the sulfate ester formed in step (a) to give a compound of formula I.

2. A process for the synthesis of a compound of formula I as defined according to claim 1 which process comprises:
(i) oxidizing a compound of formula IV

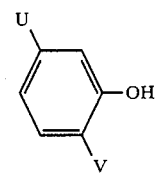

with persulfuric acid or a salt thereof to form a sulfate ester of formula II,

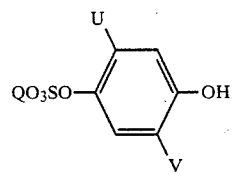

wherein Q is a cation; and
(ii) which process is characterized by the following steps in sequence:
(a) reacting the sulfate ester of formula II with a compound of formula III,

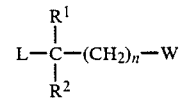

wherein L is a leaving group; and
(b) hydrolysing the sulfate ester formed in step (a) to give a compound of formula I.

3. A process according to claim 1 wherein: step (a) is carried out in the presence of a solvent and an alkaline material; and step (b) is carried out using a mineral acid or an organic acid to hydrolyse the sulfate ester.

4. A process according to claim 2 wherein:

(i) the oxidation of the compound of formula IV is carried out in aqueous alkaline solution using a salt of persulfuric acid as oxidant; and (ii) step a) is carried out in the presence of a solvent and an alkaline material; and step (b) is carried out using a mineral acid or an organic acid to hydrolyse the sulfate ester.

5. A process according to claim 1 wherein: step (a) is carried out in the presence of an organic solvent and an alkaline material chosen from the alkali metal and alkaline earth metal hydroxides and carbonates; and step (b) is carried out using a mineral acid or an organic acid to hydrolyse the sulfate ester.

6. A process according to claim 2 wherein:

(i) the oxidation of the compound of formula IV is carried out by the slow addition of a salt of persulfuric acid to an aqueous alkaline solution of the compound of formula IV; and (ii) step (a) is carried out in the presence of an organic solvent and an alkaline material chosen from the alkali metal and alkaline earth metal hydroxides and carbonates; and step (b) is carried out using a mineral acid or an organic acid to hydrolyse the sulfate ester.

7. A process according to claim 1 or claim 2 wherein: in the compound of formula (I)

U and V are independently chosen from the group consisting of hydrogen, halogen, nitro, cyano, $C_1$ to $C_6$ alkyl, $C_1$ to $C_6$ haloalkyl and $C_1$ to $C_6$ alkoxy;

$R^1$ and $R^2$ are independently chosen from hydrogen and $C_1$ to $C_6$ alkyl;

W is the group

wherein G is chosen from the group consisting of hydroxy, $C_1$ to $C_{10}$ alkoxy, $C_1$ to $C_{10}$ haloalkoxy, $C_2$ to $C_{10}$ alkenyloxy, $C_2$ to $C_{10}$ alkynyloxy, $C_1$ to $C_{10}$ alkylthio, $C_2$ to $C_{10}$ alkenylthio, $C_2$ to $C_{10}$ alkynylthio, phenoxy, benzyloxy, cyclohexyloxy, the group $C_1$ to $C_{10}$ alkoxy substituted with a substituent chosen from the group consisting of $C_1$ to $C_6$ alkoxy, amino, N-($C_1$ to $C_6$ alkyl)amino, N,N-di($C_1$ to $C_6$ alkyl)amino and N,N,N-tri($C_1$ to $C_6$ alkyl)ammonio, the group $NR^4R^5$ wherein $R^4$ and $R^5$ are independently chosen from hydrogen, $C_1$ to $C_6$ alkyl, $C_1$ to $C_6$ hydroxyalkyl, $C_1$ to $C_6$ haloalkyl, and phenyl, the group OM wherein M is an alkali metal ion, alkaline earth metal ion or an ammonium ion $HN\oplus R^7R^8R^9$ wherein $R^7$, $R^8$ and $R^9$ are independently chosen from the group consisting of hydrogen, $C_1$ to $C_6$ alkyl, $C_1$ to $C_6$ hydroxyalkyl, phenyl and benzyl, the group $-NHSO_2R^3$ wherein $R^3$ is $C_1$ to $C_6$ alkyl, and the group $-O-N=R^6$ wherein $R^6$ is a $C_1$ to $C_{10}$ alkylidene group; and n is 0;

in the compound of formula II

Q is chosen from hydrogen, the alkali and alkaline earth metals and ammonium; and in the compound of formula III L is chosen from the group consisting of chlorine, bromine, iodine, methanesulfonyl, trifluoromethanesulfonyl, p-toluenesulfonyl, methanesulfonyloxy, trifluoromethanesulfonyloxy, p-toluenesulfonyloxy, trifluoromethane sulfonamide and 1-pyrimidino p-toluenesulfonate.

8. A process according to claim 1 or claim 2 wherein:

in the compound of formula I

U and V are independently chosen from hydrogen and halogen;

$R^1$ is methyl;

$R^2$ is hydrogen;

W is the group

wherein G is chosen from the group consisting of hydroxy, $C_1$ to $C_{10}$ alkoxy, $C_2$ to $C_{10}$ alkenyloxy, $C_2$ to $C_{10}$ alkynyloxy and the group OM wherein M is an alkali metal or alkaline earth metal ion; and n is 0;

in the compound of formula II

Q is an alkali metal or ammonium; and in the compound of formula III

L is chosen from the group consisting of chlorine bromine and iodine.

9. A process according to claim 1 or claim 2 wherein:

in the compound of formula I

U and $R^2$ are both hydrogen;

V is chosen from hydrogen;

$R^1$ is methyl;

W is the group

wherein G is chosen from the group consisting of hydroxy, $C_1$ to $C_6$ alkoxy and OM wherein M is an alkali metal ion; and n is 0;

in the compound of formula II

Q is chosen from sodium, potassium and ammonium; and in the compound of formula II L is chosen from the group consisting of chlorine, bromine and iodine.

10. A process according to claim 1 or claim 2 where the compound of formula I is chosen from 2-(4-hydroxyphenoxy)propionic acid and the methyl, ethyl, n-propyl, n-butyl, isobutyl and secondary butyl esters thereof.

* * * * *